United States Patent
Suzuki

(10) Patent No.: US 8,002,696 B2
(45) Date of Patent: Aug. 23, 2011

(54) ENDOSCOPE SYSTEM

(75) Inventor: Keita Suzuki, Tokyo (JP)

(73) Assignee: Olympus Corporation (JP)

( * ) Notice: Subject to any disclaimer, the term of this patent is extended or adjusted under 35 U.S.C. 154(b) by 492 days.

(21) Appl. No.: 11/873,507

(22) Filed: Oct. 17, 2007

(65) Prior Publication Data

US 2008/0103358 A1    May 1, 2008

Related U.S. Application Data

(63) Continuation of application No. PCT/JP2005/017530, filed on Sep. 22, 2005.

(51) Int. Cl.
*A61B 1/00* (2006.01)
(52) U.S. Cl. .................... 600/106; 600/104
(58) Field of Classification Search ............ 600/106, 600/131, 154, 104, 124, 125; 604/159
See application file for complete search history.

(56) References Cited

U.S. PATENT DOCUMENTS

| | | | | |
|---|---|---|---|---|
| 4,383,532 | A * | 5/1983 | Dickhudt | 607/117 |
| 5,060,632 | A * | 10/1991 | Hibino et al. | 600/109 |
| 5,251,356 | A * | 10/1993 | Oaki et al. | 15/104.095 |
| 5,346,498 | A * | 9/1994 | Greelis et al. | 606/108 |
| 6,129,661 | A * | 10/2000 | Iafrati et al. | 600/121 |
| 6,171,234 | B1 * | 1/2001 | White et al. | 600/102 |
| 6,290,675 | B1 * | 9/2001 | Vujanic et al. | 604/159 |
| 6,726,675 | B1 * | 4/2004 | Beyar | 604/510 |
| 7,736,300 | B2 * | 6/2010 | Ziegler et al. | 600/114 |
| 2005/0171478 | A1 | 8/2005 | Selmon et al. | |

FOREIGN PATENT DOCUMENTS

| | | |
|---|---|---|
| EP | 1 568 305 A1 | 8/2005 |
| JP | S57-117823 | 7/1982 |
| JP | 58-008028 | 1/1993 |
| JP | 9-492 | 1/1997 |
| JP | 11-225942 | 8/1999 |
| JP | 2003-265406 | 9/2003 |
| JP | 2005-211205 | 8/2005 |
| JP | 2005-237660 | 9/2005 |

OTHER PUBLICATIONS

Office Action issued by the Japanese Patent Office on Feb. 16, 2010 in connection with corresponding Japanese application No. 2004-084438.
English translation of Office Action issued by Japanese Patent Office on Feb. 16, 2010 in connection with Japanese application No. 2004-084438.

(Continued)

*Primary Examiner* — Matthew J Kasztejna
*Assistant Examiner* — Alireza Nia
(74) *Attorney, Agent, or Firm* — Ostrolenk Faber LLP

(57) ABSTRACT

An endoscope system has an driving-section for driving an insertion-section having an instrument. The driving-section is supported by a pivoting section rotatively. The driving-section has two rollers facing each other. The insertion-section is disposed between the rollers. The insertion-section is extended or retracted by rotating the rollers if the rollers are disposed with respect to the extension/retraction direction. If the pivoting section is pivoted to be orthogonal to the extension/retraction direction, the insertion-section rotates around its axial line by the rotation of the rollers. By doing this, it is possible to rotate the instrument easily in the endoscope system for extending/retracting the instrument by electric power.

8 Claims, 10 Drawing Sheets

OTHER PUBLICATIONS

International Search Report and Written Opinion in Japanese in corresponding PCT Appln. No. PCT/JP2005/017530 dated Oct. 25, 2005.
English Translation of International Search Report in corresponding PCT Appln. No. PCT/JP2005/017530 dated Oct. 25, 2005.
Search Report issued by European Patent Office in connection with corresponding application No. EP 05 78 5855 on Oct. 18, 2010.
Japanese Office Action mailed Mar. 29, 2011 in connection with corresponding Japanese Patent Application No. 2004-084438.
Partial English translation of Japanese Office Action issued in connection with corresponding Japanese application provided as an explanation of prior art relevancy.

* cited by examiner

ENDOSCOPE SYSTEM

CROSS-REFERENCE TO RELATED APPLICATION

This is a Continuation Application of International Application No. PCT/JP2005/017530, filed Sep. 22, 2005, which claims priority on Japanese Patent Application No. 2004-084438 (filed on Mar. 23, 2004). The contents of the aforementioned application are incorporated herein by reference.

BACKGROUND OF THE INVENTION

1. Field of the Invention

The present invention relates to an endoscope system inserted into a human body.

2. Description of the Related Art

Endoscopes are known for inserting thereof into human cavities to inspect alimentary canal. In order to inspect the inside of human cavities, an endoscope has a flexible insertion section and a charge-coupled-device formed on a distal end of the insertion section. A channel penetrates through a proximal end and distal end of the endoscope so that the distal end is inside the human cavities and the proximal end is outside the human cavities. Various treatments can be conducted by inserting instruments, e.g., a pair of forceps into the channel.

Endoscope systems are under development in which instruments are extended and retracted by several pairs of rollers, driven by electricity, which are disposed in the endoscope (refer to Japanese Unexamined Patent Application, First Publication No. S57-117823, for example). According to this type of endoscope systems, an instrument is supported by the circumference of a pair of rotative drums driven by micro-motors which are provided in the endoscope. The instrument supported between the drums can be extended from the channel and retracted into the channel by operating, i.e., rotating the drums electrically by operating the micromotors in predetermined directions.

SUMMARY OF THE INVENTION

An object of the present invention is to provide an endoscope system having an instrument so that the instrument can be not only extended and retracted with respect to human cavities but also rotated around an axis of the channel mechanically.

A first aspect of the present invention is an endoscope system which includes: an endoscope having a channel; an insertion-section flexibly inserted into the channel; an instrument inserted into the insertion-section; a treating section, disposed at a distal end of the instrument, for treating a target section; an driving-section, making contact with the insertion-section, for driving the insertion-section with respect to predetermined directions; and a pivoting section for directing the driving-section toward a first direction or a second direction, so that the first direction indicates the direction for driving the insertion-section along an axial line of the insertion-section, and the second direction indicates the direction for rotating the insertion-section around the axial line.

This aspect of the endoscope system has at least the pivoting sections for directing the driving-section so that the instrument is extended from the channel and retracted into the channel by the driving-section when the driving-section is driven with respect to the first direction. The instrument is rotative around the axis by driving the driving-section, i.e., changing the direction of the driving-section by 90 degrees, from the first direction to the second direction while the instrument is inserted in the channel.

In a second aspect of the present invention, the pivoting section directs the driving-section from 0 to 90 degrees with respect to the axial line.

In this aspect of the endoscope system, the driving-section can be directed in two directions, i.e., 0 (zero) degrees and 90 (ninety) degrees with respect to the axis; therefore, the instrument can be driven with respect to the axial direction and the circumferential direction around the axis.

In a third aspect of the present invention, the driving-section has a plurality of rollers making contact with the insertion-section.

This aspect of the endoscope system has the rollers; therefore, it is possible to drive the insertion-section reliably by a simple structure.

In a fourth aspect of the present invention, the driving-section includes: the plurality of rollers; and a switching section for changing the rotational direction of at least one of the rollers in accordance with the pivoted direction of the rollers.

This aspect of the endoscope system has the switching section to set the direction for rotating the rollers in accordance with the driving direction of the insertion-section. Therefore, it is possible to extend, retract, and rotate the instrument reliably.

In a fifth aspect of the present invention, protrusions are formed on outer surfaces of the rollers.

In this endoscope system, it is possible to prevent the rollers from slipping on the insertion-section because the protrusions and grooves are formed on the rollers in this aspect of the endoscope system. Therefore, it is possible to extend, retract, and rotate the instrument reliably.

In a sixth aspect of the present invention, the endoscope system further includes: a housing for pivotably supporting the driving-section; and a guide member, fixed in the housing, through which the insertion-section is inserted, the guide member having apertures through which the driving-section making contact with the insertion-section.

In this endoscope system, positioning of the insertion-section is regulated by the guide member; therefore, it is possible to maintain the contact between the insertion-section and the driving-section easily even if the direction of the driving-section is changed.

In a seventh aspect of the present invention, protrusions and grooves are alternately provided on a surface of the insertion-section, the surface making contact with the driving-section.

In this aspect of the endoscope system, the protrusions and grooves are formed on the surface of the insertion-section; therefore, it is possible to maintain the contact between the insertion-section and the driving-section easily even if the direction of the driving-section is changed.

In an eighth aspect of the present invention, a cross section of a part of the insertion-section is polygonal, the part making contact with the driving-section.

In this aspect of the endoscope system, the cross section of a part of the insertion-section is polygonal; therefore, it is possible to maintain the contact between the insertion-section and the driving-section easily even if the direction of the driving-section is changed.

In a ninth aspect of the present invention, each pivoting section has a pivoting shaft having a pivoting axial line, the pivoting axial line being disposed on a line extending along radial directions of the rollers, and passes through a section in which the rollers making contact with the insertion-section.

In this aspect of the endoscope system, the driving-section rotates around a section in which the rollers make contact with the insertion-section; therefore the contact between the rollers and the insertion-section can be maintained when the driving direction of the insertion-section changes between the first direction and the second direction.

A tenth aspect of the endoscope system includes: a channel formed in the endoscope system; an insertion-section flexibly inserted into the channel; a treating section, disposed on a distal end of the insertion-section, for treating a target section, the treating section being manipulated by a wire disposed in the insertion-section; an driving-section for driving the insertion-section with respect to predetermined directions, the driving-section making contact with the insertion-section; a wire driving section for driving the wire with respect to the predetermined directions; and a pivoting section for directing the driving-section and the wire-driving section with respect to first and second directions, so that the first direction indicates the direction for driving the driving-section and the wire along the axial lines thereof, and the second direction indicates a circumferential direction with respect to the axial line.

This aspect of the endoscope system includes the driving-section; and the wire driving section so that the insertion-section and the wire are driven separately. In addition, it is possible to change the direction of the driving-section and the direction of the wire driving section by the pivoting sections. The instrument is extended and retracted when the driving-section and the wire driving section are driven with respect to the first direction. Also, the instrument rotates around the second direction when the driving-section and the wire driving section are driven with respect to the second direction.

An eleventh aspect of the present invention is the endoscope system which further includes a tube connected to a proximal end of the insertion-section, wherein the wire is inserted in the tube, and the tube make contact with the wire-driving section.

The tube, through which the wire is inserted, is driven by the wire driving section; therefore, the wire can be fed in forward and rear directions and rotated around an axis of the wire in this aspect of the endoscope system.

A twelfth aspect of the present invention is the endoscope system which further includes a control section for controlling the driving-section and the wire-driving section, wherein the control section has selective modes, the modes including: a first mode in which the driving-section and the wire-driving section are driven synchronously; and a second mode in which the wire-driving section is driven while the driving-section is stopped In this aspect of the endoscope system, the insertion-section and the wire are driven with respect to the same direction synchronously when the first mode is selected. In contrast, only the wire is driven while the insertion-section is stopped when the second mode is selected.

A thirteenth aspect of the present invention is an endoscope system which includes: an endoscope having a channel; an insertion-section flexibly inserted into the channel; a treating section, disposed at a distal end of the insertion-section, for treating a target section; an driving-section, making contact with the insertion-section, for driving the insertion-section along an axial line of the channel; and a rotative-connective section for connecting the driving-section and the endoscope so that the driving-section is rotative around the axial line of the channel.

In this aspect of the endoscope system, the driving-section drives the insertion-section along the axial line of the channel. When the driving-section is rotated while the insertion-section is inserted in the channel, the driving-section and the insertion-section rotate around the axis of the channel; as a result of this rotation, the instrument rotates around its axis.

According to the present invention, in the endoscope system in which the instrument is extended and retracted by the driving-section, the driving direction of the insertion-section can be changed by changing the direction of the driving-section. Therefore, it is possible to extend the instrument from the channel, retract the instrument into the channel, and rotate the instrument around the axis of the instrument easily.

DETAILED DESCRIPTION OF THE INVENTION

Preferable embodiments for carrying out the present invention are explained in details with reference to the drawings as follows.

Figure 1:
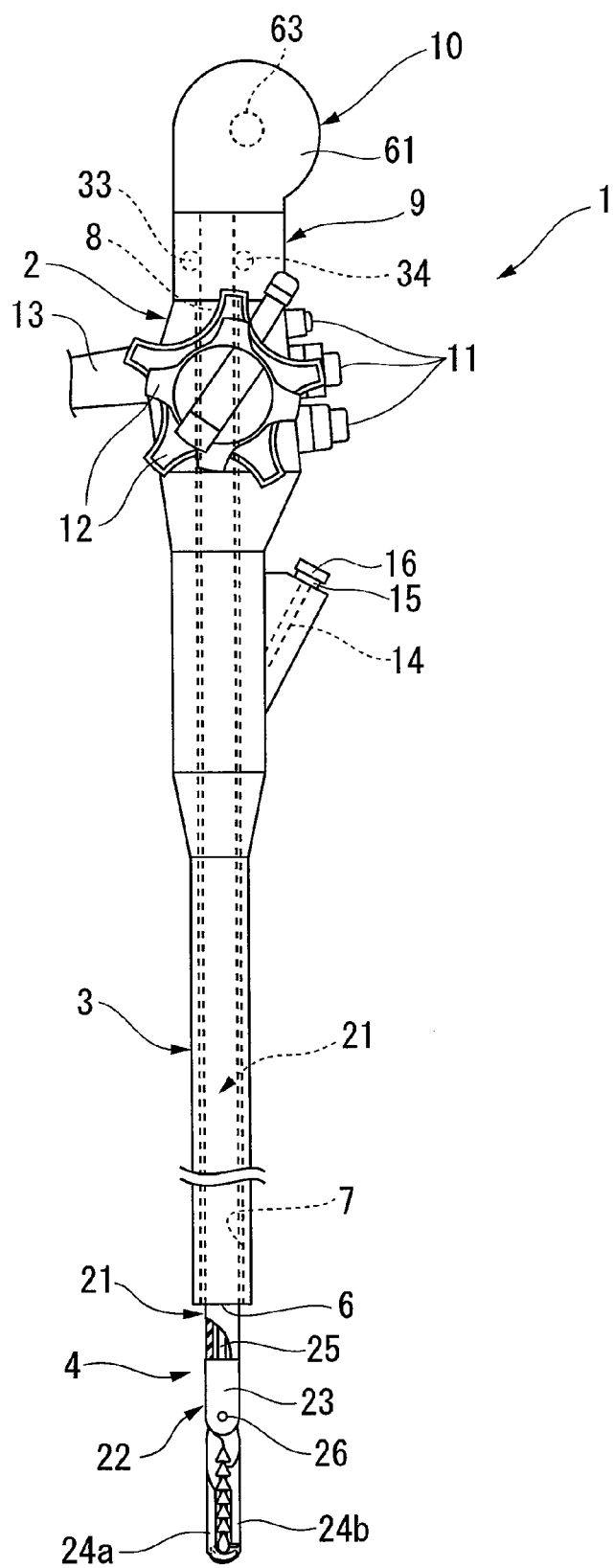
FIG. 1 is an overall view of the endoscope system according to embodiments of the present invention.

FIG. 1 is a view showing a general structure of an endoscope system according to a first embodiment.

As shown in FIG. 1, an endoscope 1 has an operation section 2 which is operated by an operator, e.g., a surgeon, and a flexible insertion section 3 which is formed on a distal end of the operation section 2 so that the insertion section 3 can be inserted into human cavities. An optical system, not shown in the drawing, which is used for, e.g., image-capturing and lighting purposes is disposed on a distal end of the insertion section 3. Furthermore, on a distal end of the insertion section 3, a distal aperture 6 of the instrument channel 7 is formed into which an instrument 4 is inserted. The instrument channel 7 communicates through the endoscope 1 from the distal end of the insertion section 3 to a proximal end of the operation section 2. An insertion port 8, into which the instrument 4 is inserted, is formed on the proximal end of the operation section 2. An enclosure device 10 for containing the instrument 4 is attached to the proximal end of the operation section 2 via an instrument-extension-retraction device 9.

Switches 11 for switching lighting beams and knobs 12 for changing the directions of the distal end of the insertion section 3 are disposed on an outer surface of the operation section 2. A universal cable 13, connected to a system main body which is not shown in the drawing, is connected to a side portion of the operation section 2. An insertion port 15 into which another instrument channel 14 is inserted, is formed beneath the switches 11 so that the insertion port 15 and the switches 11 are disposed on the same side of the operation section 2. A cap 16 can be attached for sealing the insertion port 15. The instrument channel 14 and the insertion port 15 are not indispensable in the present invention.

FIG. 1 shows a pair of forceps as an example of the instrument 4. The instrument 4 has an insertion-section 21 which is inserted in the instrument channel 7. The insertion-section 21 has a sheath which is formed by covering a dense coil with a resin-coated tube so that a wire 25 can be inserted in the sheath. A treating section 22 is disposed on a distal end of the insertion-section 21. The treating section 22 includes a distal end cover (e.g., a supporting member) 23 fixed on a distal end of the insertion-section 21, a pair of gripping members 24a and 24b supported by the distal end cover 23 rotatively, and a link mechanism (not shown in the drawing) for rotating the gripping members 24a and 24b. A distal end of the link mechanism is connected to the gripping members 24a and 24b and another distal end thereof is connected to a distal end of the wire 25. That is, the gripping members 24a and 24b of the instrument 4 open at a center of a shaft 26 by feeding the wire 25 toward the instrument 4. The gripping members 24a and 24b of the instrument 4 close at a center of the shaft 26 by winding the wire 25 into the enclosure device 10.

The wire 25 is inserted in the insertion-section 21. The wire 25 and the insertion-section 21 are inserted in the instrument channel 7 so that both of which can be extracted from the insertion port 8 formed on the proximal end of the operation section 2. The wire 25 and the insertion-section 21 are further disposed in the instrument-extension-retraction device 9 and wound by the enclosure device 10.

Figure 2:
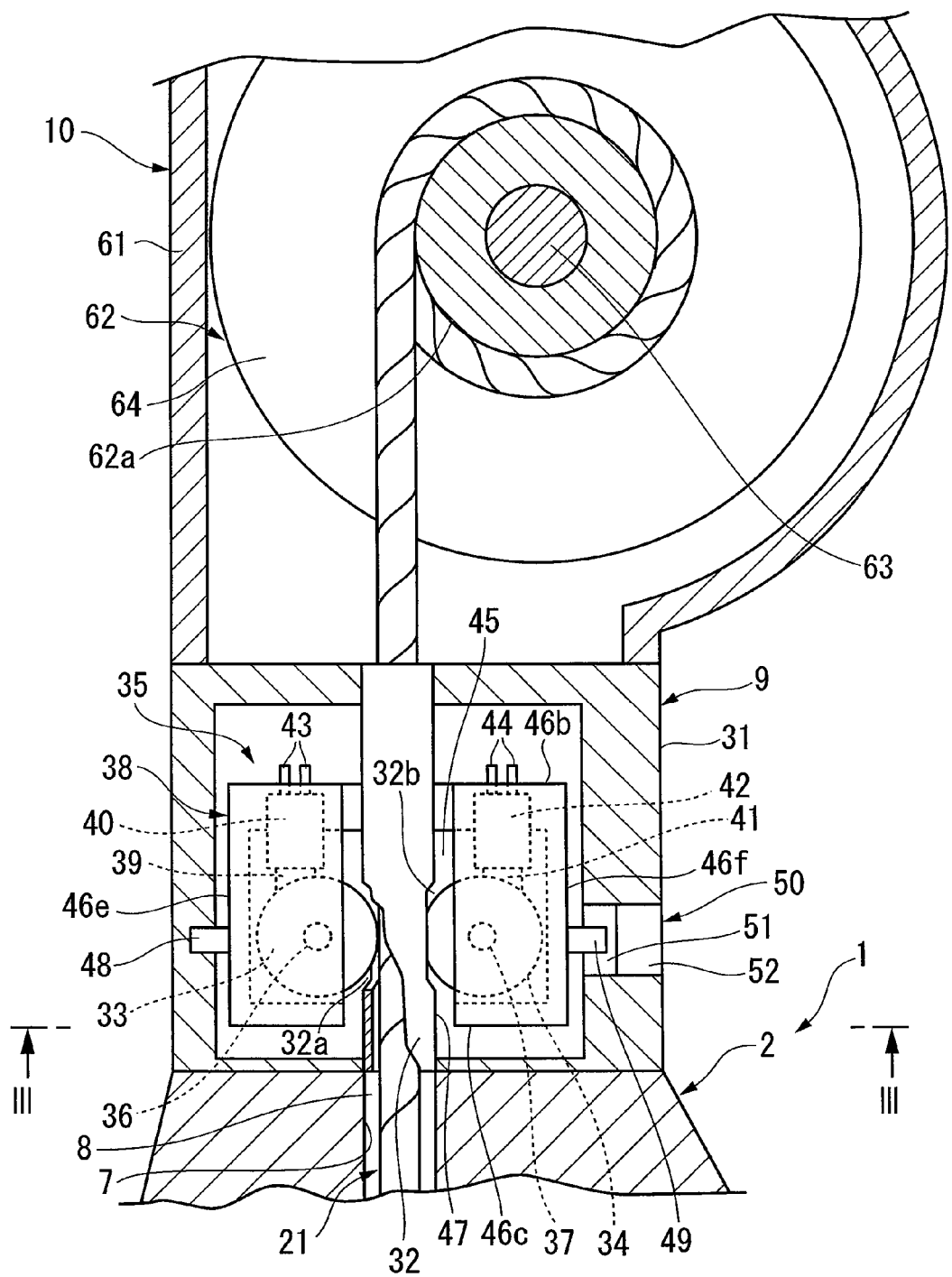
FIG. 2 shows a part of a cross section of the endoscope system.

As shown in FIG. 2, the instrument-extension-retraction device 9 has a housing 31 which is fixed on the proximal end of the operation section 2. A hollow guide member 32 is fixed in the housing 31. An axis of the guide member 32 coincides with an axis of the instrument channel 7. The insertion-section 21 is inserted in the guide member 32. Two aperture sections 32a and 32b are formed in the middle of the guide member 32 from which the insertion-section 21 is exposed. Outer circumferential portions of a pair of rollers 33 and 34 are partly inserted into the guide member 32 through these aperture sections 32a and 32b.

These rollers 33 and 34 form an driving-section 35 so that the insertion-section 21 is disposed between the rollers. Rotation axes 36 and 37 of the rollers are supported rotatively by roller supporting sections 38 through bearings (not shown in the drawing). Rotation axes 36 and 37 are disposed in parallel so that each axis is orthogonal with the axial line (i.e., with respect to the insertion-retraction direction) of the instrument channel 7.

A transmission mechanism 39 is connected to the rotation axis 36 of the roller 33. The transmission mechanism 39 includes gears, etc., so that the transmission mechanism 39 decelerates rotation of a motor 40 and transmits the rotation to the rotation axis 36. Similarly, a transmission mechanism 41 is connected to the rotation axis 37 of the roller 34. The transmission mechanism 41 decelerates rotation of a motor 42 and transmits the rotation to the rotation axis 37. The motors 40, 42 and the transmission mechanisms 39, 41 are fixed to a roller supporting section 38. Terminals 43, 44 used for conducting electricity are disposed from the motors 40 and 42 respectively. Each terminal 43 and 44 has distal ends protruding outside to the roller supporting section 38 and the distal ends are connected to a power supply by power cables which are not shown in the drawing.

Figure 3:
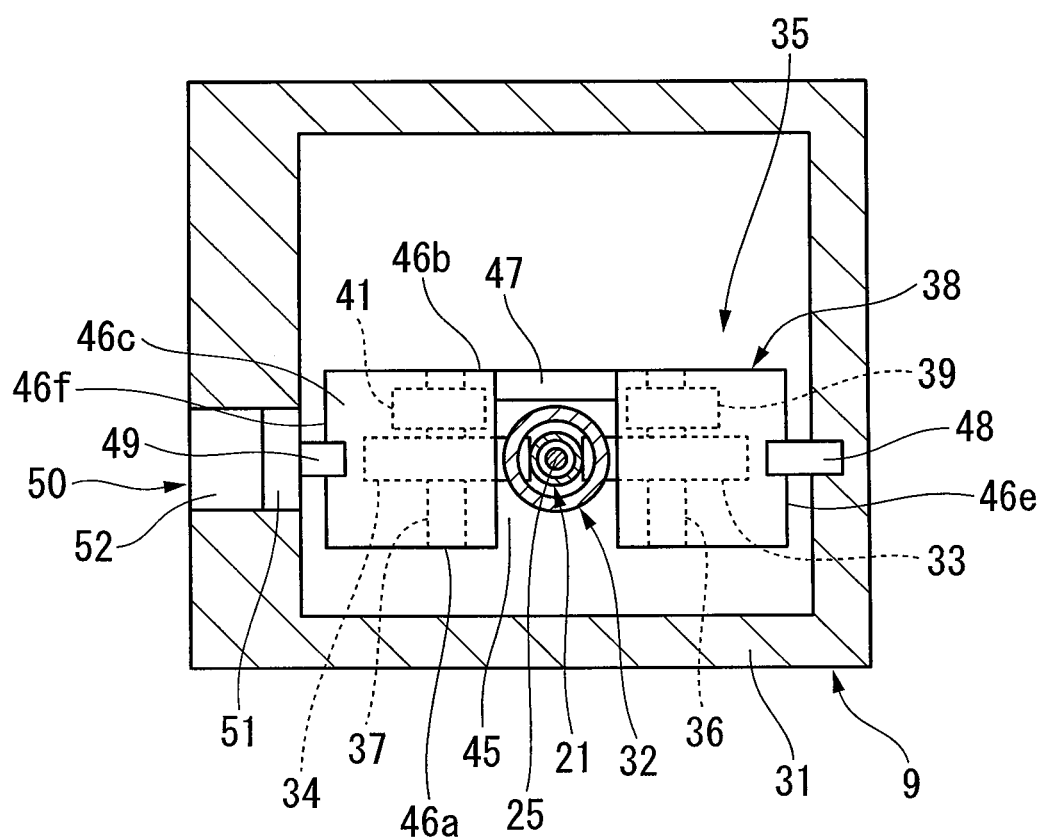
FIG. 3 is a cross section viewed along a line III-III of FIG. 2 where the driving-section corresponds to the first direction.
Figure 5:
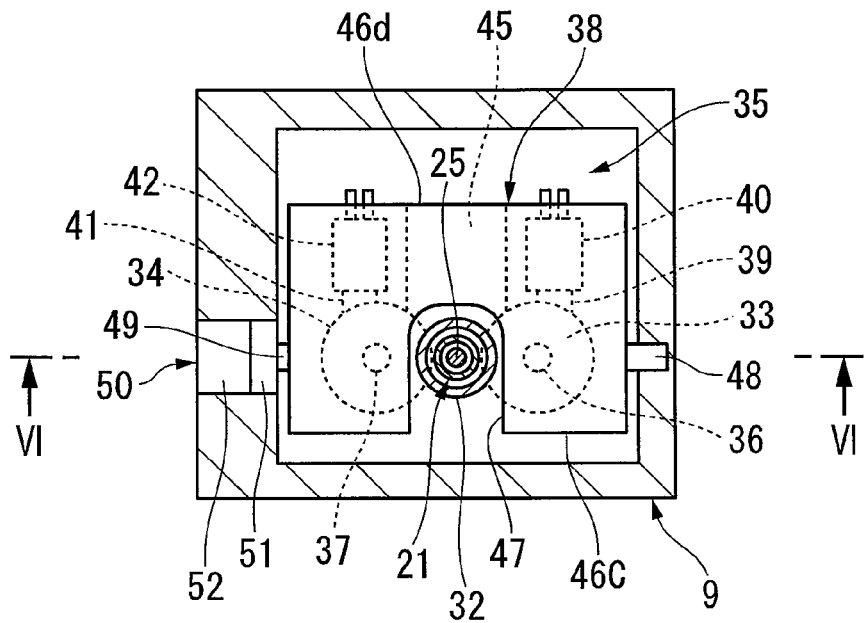
FIG. 5 is a view where the direction of the driving-section is changed by 90 degrees from the state shown in FIG. 3.

As shown in FIG. 3, a groove 45 is formed in an approximate center of the roller supporting section 38 so that the insertion-section 21 and the guide member 32 are disposed in the groove 45. The groove 45 has openings to side surfaces 46a of the roller supporting section 38 while a side surface 46b of the roller supporting section 38 is closed. An opening section of the grooves 45 on the side surfaces 46a is greater than an outer diameter of the guide member 32. Also, as shown in FIGS. 2 and 5, the groove 45 extends from a front surface 46c of the roller supporting section 38 to a back surface 46d.

As shown in FIG. 3, a portion of another side surface 46b near the front surface 46c is cut off so that the cut-off section 47 has a corresponding shape with the side surface 46b closing the groove 45. A width of the cut-off section 47 is approximately equal to a width of the groove 45. A length of the cut-off section 47 is longer than a distance between the front surface 46c and a line passing through the rotation axes 36 and 37 as rotation centers of the rollers 33 and 34. The length of the cut-off section 47 is shorter than a distance between the front surface 46c and the back surface 46d.

Rotation axes 48 and 49, by which the roller supporting section 38 is rotative, are fixed to a top surface 46e and a bottom surface 46f respectively. The pivoting section 50 includes these rotative axes 48 and 49.

The pivoting section 50 includes the rotation axes 48, 49, a transmission mechanism 51 for rotating the rotation axis 49, and a motor 52. The rotation axes 48 and 49 are disposed on a predetermined line. The predetermined line is formed by radial lines of the rollers 33 and 34 so that the predetermined line passes points at which the rollers 33 and 34 make contact with the insertion-section 21. The rotation axis 48 is rotatively supported by a bearing (not shown in the drawing) in the housing 31. The rotation axis 49 is connected to the motor 52 via the transmission mechanism 51. The transmission mechanism 51 includes gears, etc., so that the transmission mechanism 51 decelerates rotation of the motor 52 and transmits the rotation to the rotation axis 49. The motor 52 is fixed to the housing 31 so that the driving-section 35, including the roller supporting section 38, and the rollers 33 and 34, rotates around an axis defined by the rotation axes 48 and 49 by approximately 90 degrees by driving (i.e., rotating) the rotation axis 49.

Figure 4:
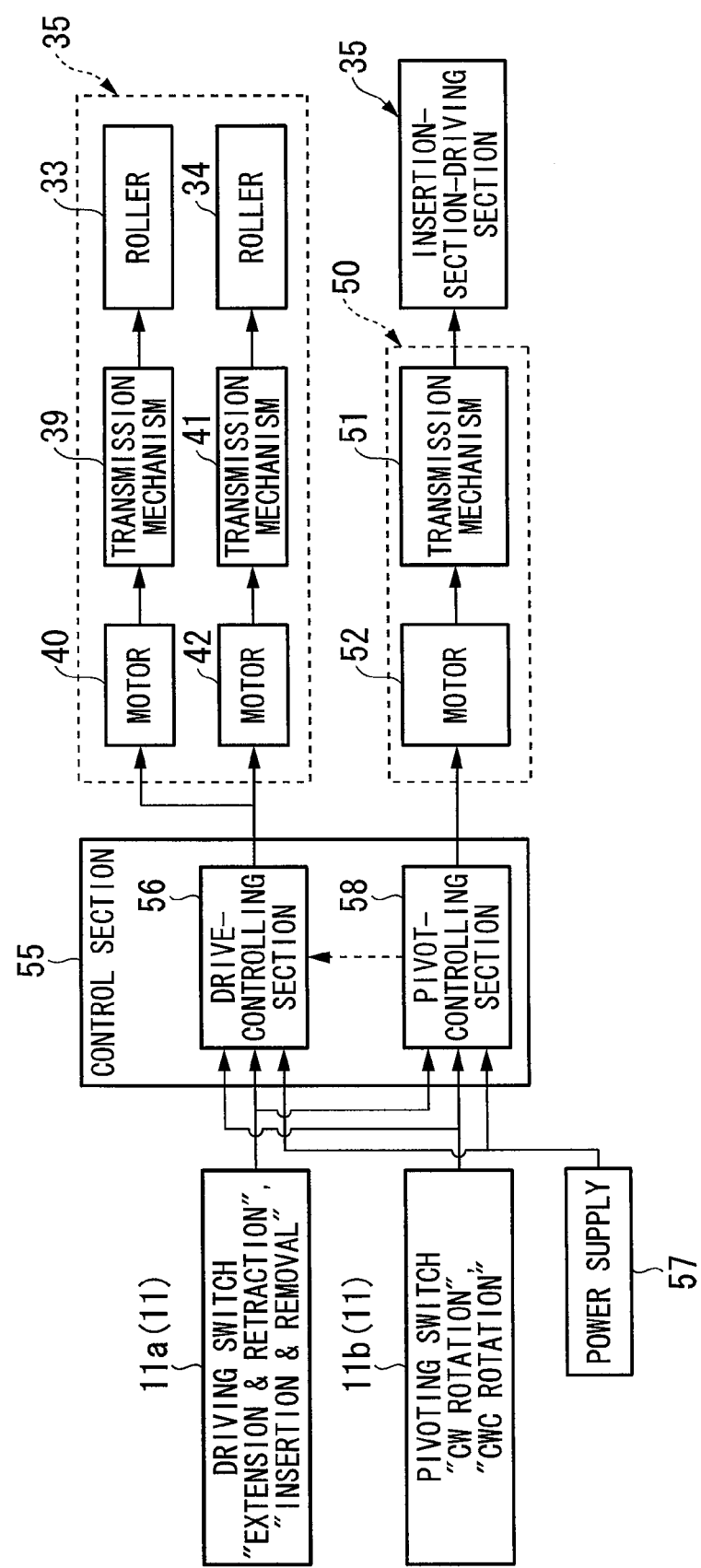
FIG. 4 is a control block diagram according to the present invention.

FIG. 4 is a control block diagram for controlling the motors 40, 42 contained in the driving-section 35 and the motor 52 contained in the pivoting section 50.

Switches 11 formed on the operation section 2 of the endoscope 1 include a driving switch 11a for driving the rollers 33 and 34 contained in the driving-section 35, and a pivoting switch 11b for driving the motor 52 contained in the pivoting section 50. The driving switch 11a can perform "inserting the instrument 4 into the instrument channel 7", "retracting the instrument 4 from the instrument channel 7", "extending the instrument 4 through the instrument channel 7", and "retracting the instrument 4 through the instrument channel 7". The driving switch 11a is connected to a drive-controlling-section (driver circuit) 56 and a pivot-controlling-section (driver circuit) 58 which are contained in the operation section 2.

The pivoting switch 11b can perform "clockwise rotation of the instrument 4" and "counterclockwise rotation of the instrument 4". The pivoting switch 11b is connected to the drive-controlling-section 56 and the pivot-controlling-section 58.

The drive-controlling-section 56 is connected to a power supply 57 and the motors 40 and 42. The drive-controlling-section 56 controls rotation of the motors 40 and 42 in accordance with operation results of the driving switch 11*a* and the pivoting switch 11*b*. The drive-controlling-section 56 can control rotation directions of the rollers 33 and 34 independently. Parameters for controlling the rotation directions of the rollers 33 and 34 are a direction of the instrument 4 determined by the operator of the endoscope, and a direction of the driving-section 35.

The pivot-controlling-section 58 is connected to a power supply 57 and the motor 52. The pivot-controlling-section 58 controls rotation of the motor 52 in accordance with operation results of the driving switch 11*a* or the pivoting switch 11*b*.

The control section 55 is an element for forming the driving-section 35. The control section 55 is preferably disposed in the instrument-extension-retraction device 9. The control section 55 may be disposed in the operation section 2 of the endoscope 1.

The enclosure device 10 is fixed on the proximal end of the instrument-extension-retraction device 9 having the above structure.

The enclosure device 10 has a reel cover 61 which covers an aperture formed on the proximal end of the instrument-extension-retraction device 9. A reel 62 is supported rotatively in the reel cover 61.

A rotation axis 63 as a rotation center of the reel 62 is disposed offset from an axial line of the instrument channel 7. The rotation axis 63 is approximately orthogonal to the axial line of the instrument channel 7. The rotation axis 63 is offset to the axis of the instrument channel 7 so that the instrument 4 wound around the reel 62 is fed into the instrument-extension-retraction device 9 smoothly. In the present embodiment, the rotation axis 63 is disposed opposite the universal cable 13 with respect to the axis of the instrument channel 7.

The reel 62 has flange sections 64, having greater diameters than a wire-winding section, disposed on both ends of the rotation axis 63. The insertion-section 21 having the instrument 4 is wound around an outer surface 62*a* of the reel 62 which is located between two flange sections 64.

Operations in the present embodiment are explained as follows. An initial position of the driving-section 35 is shown in FIG. 2 where the axis passing through the rotation axes 36, 37 of the rollers 33, 34 is orthogonal to the axis (first direction) of the instrument channel 7. Most of the insertion-section 21 is wound in the enclosure device 10. A part of the treating section 22 is inserted into the instrument channel 7 from its insertion port 8. The pair of the rollers 33 and 34 which are contained in the driving-section 35 are pressed to the distal end of the insertion-section 21.

The instrument 4 is inserted into the instrument channel 7 by moving the driving-section 35 using the driving switch 11*a* (see FIG. 4) so that the insertion-section 21 is fed toward the distal end of the endoscope 1. In this case, the drive-controlling-section 56 shown in FIG. 4 receives information sent from the pivot-controlling-section 58 and confirms that the driving-section 35 is disposed in the first direction. After the confirmation, the drive-controlling-section 56 outputs driving signals to the motors 40 and 42. By doing this, the roller 33 rotates in a clockwise direction viewed in FIG. 2 by the motor 40 and the transmission mechanism 39. The roller 34 rotates in a counterclockwise direction viewed in FIG. 2 by the motor 42 and the transmission mechanism 41. The insertion-section 21 disposed between a pair of the rollers 33 and 34 is fed, as if the insertion-section 21 is pushed by the rollers, into the instrument channel 7 toward the distal end of the endoscope 1. The motors 40 and 42 are stopped after a predetermined length of the treating section 22 protrudes from the distal end of the endoscope.

When retracting the instrument 4 from the instrument channel 7 using the driving-section 35, the moving direction of the driving switch 11*a* is set as "retraction". Then, the rollers 33 and 34 rotate opposite to the feeding direction so that the insertion-section 21 is retracted and wound into the enclosure device 10. The distal end of the insertion-section 21 is not wound into the enclosure device 10.

Extension/retraction movement of the treating section 22 supported by the instrument 4 inserted in the instrument channel 7 can be conducted similarly to the insertion of the instrument 4 into the instrument channel 7 and the retraction of the instrument 4 from the instrument channel 7.

The instrument 4 can be rotated around its axial line by operating the pivoting switch 11*b* (see FIG. 4) after inserting the instrument 4 into the instrument channel 7. By doing this, a direction of the driving-section 35 is changed by the pivoting section 50, and after that, the pivoted driving-section 35 starts moving.

That is, the driving-section 35 outputs the driving signals from the pivot-controlling-section 58 (see FIG. 4) to the motor 52; thus, the driving-section 35 rotates around the rotation axes 48 and 49. By doing this, the roller supporting section 38 rotates around a section where the insertion-section 21 makes contact with the rollers 33 and 34 while the positions of the guide member 32 and the insertion-section 21 remain the same.

Figure 6:
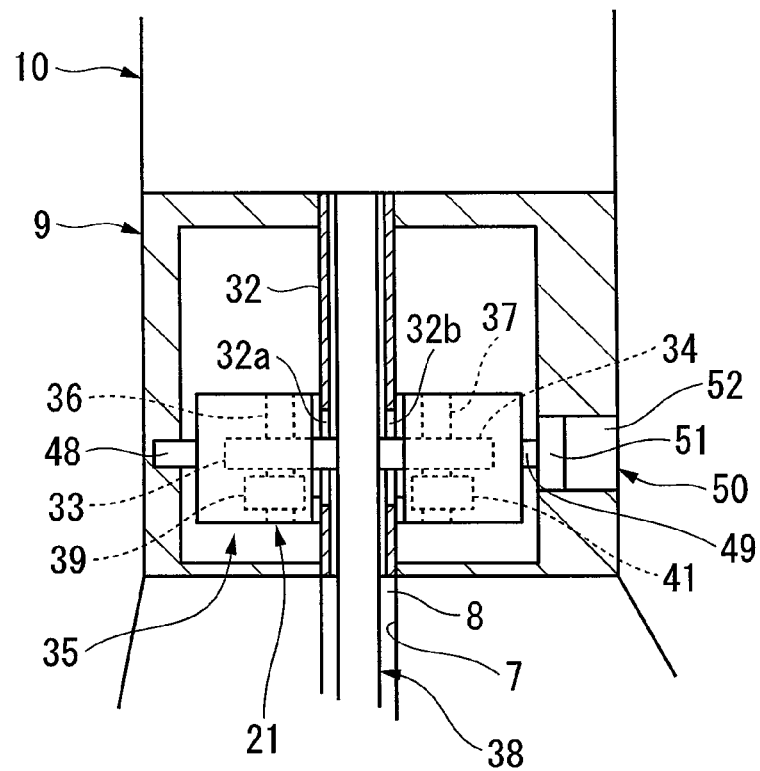
FIG. 6 is a cross section viewed along a line VI-VI shown in FIG. 5.

As shown in FIGS. 5 and 6, the pivot-controlling-section 58 stops the motor 52 after the driving-section 35 rotates by 90 degrees. This state indicates the second direction in which an axis of the driving-section 35, passing through the rotation axes 36 and 37 of the rollers 33 and 34, is in parallel with the axis of the instrument channel 7. That is, rotating directions of the rollers 33 and 34 are orthogonal to the axial direction of the insertion-section 21. Therefore, when the driving-section 35 is driven in this state, the insertion-section 21 rotates around its axis by the rotating rollers 33 and 34. When the treating section 22 (see FIG. 1) rotating with the insertion-section 21 is in a preferable rotating position for treating a target section, the pivoting switch 11*b* is turned off so as to stop the driving-section 35.

The driving-section 35 rotates the rollers 33 and 34 in the counterclockwise direction viewed in FIG. 5 so as to rotate the instrument 4 in the clockwise direction. The driving-section 35 rotates the rollers 33 and 34 in the clockwise direction viewed in FIG. 5 so as to rotate the instrument 4 in the counterclockwise direction. Directions for rotating the rollers 33 and 34 are determined by the drive-controlling-section 56 in accordance with switching operations conducted by the operator of the endoscope, information obtained from the pivot-controlling-section 58 with respect to directions of the driving-section 35, and the results of retrieving a predetermined table which defines the rotation directions of the motors 40 and 42. Instead of switching the rotating directions of the motors 40 and 42, the rotating directions of the rollers 33 and 34 may be switched by mechanical operations, e.g., changing the gear combination in the transmission mechanisms 39 and 41 by the drive-controlling-section 56. Controlling of the pivot-controlling-section 58 is skipped when only the rotation direction of the instrument 4, etc., around its axial direction is changed because the driving-section 35 is in the second direction; thus, only the drive-controlling-section 56 moves.

If the driving switch 11*a* is turned on in a state such that the instrument 4 is rotated in clockwise or counterclockwise direction, i.e., in a state such that the driving-section 35 is disposed in the second direction, the pivot-controlling-section 58 starts the motor 52 contained in the pivoting section 50 so that direction of the driving-section 35 is changed to the first direction. After changing the direction of the driving-section 35, the drive-controlling-section 56 starts so as to rotate the rollers 33 and 34 in a required direction.

According to the present embodiment, the endoscope system permitting the insertion-section 21 to move electrically has a pivoting section 50 which can change the directions of the rollers 33 and 34 used to extend/retract the instrument 4. Therefore, it is possible to rotate the instrument 4 around its axis easily.

The pivoting section 50 pivots the rollers 33 and 34 at the center where the rollers 33, 34 make contact with the insertion-section 21; therefore, it is possible to maintain the contact between the rollers 33, 34 and the insertion-section 21 reliably. Also, since the insertion-section 21 is inserted in the guide member 32, the insertion-section 21 does not deviate from between the rollers 33 and 34 while changing the directions of the rollers 33 and 34.

Examples of a structure or method for preventing such slippage or deviation of the insertion-section 21 from between the rollers 33 and 34 may be as follows.

Figure 7A:
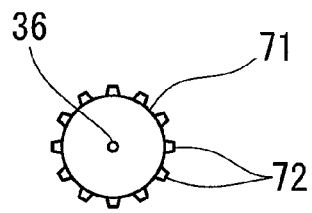
FIG. 7 is a view showing an example of rollers.
Figure 7B:
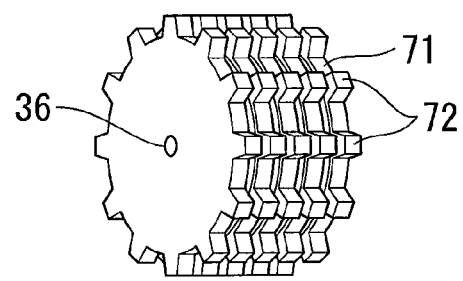

As shown in FIG. 7, protrusions 72 may be formed on an outer surface of a roller 71. The protrusions 72 expand in a width direction of the roller 71. Several grooves may be formed on the outer surface of the roller 71 in its rotation direction. It is possible to increase friction between the outer circumference of the roller 71 and the insertion-section 21 by forming protrusions or grooves on the outer surface of the roller 71.

Figure 8:
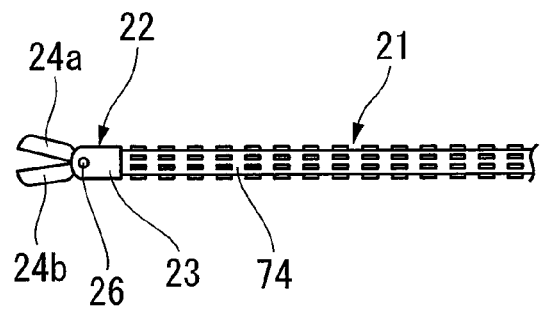
FIG. 8 is a view showing an example of the insertion-section.

As shown in FIG. 8, the insertion-section 21 may be a coil 74 formed by densely winding a resin-made wire having protrusions on its surface. It is possible to increase friction between the outer surfaces of the rollers 33, 34 and the insertion-section 21 by forming protruding patterns on the outer surface of the insertion-section 21.

Figure 9A:
FIG. 9 is a view showing an example of a cross section of the insertion-section.
Figure 9B:
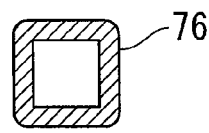
Figure 9C:
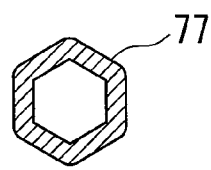

Friction between the outer surface of the rollers 33, 34 and the insertion-section 21 may increase by modifying the cross section of the insertion-section 21. More specifically, as shown in FIGS. 9A to 9C, an insertion-section 75 may have a triangular cross section (FIG. 9A); an insertion-section 76 may have a rectangular cross section (FIG. 9B); and an insertion-section 77 may have a hexagonal cross section (FIG. 9C). In these cases, the insertion-sections 75, 76, and 77 are produced by winding the resin-made wire around cores (not shown in the drawings) having cross sections corresponding to the above shapes.

Figure 10:
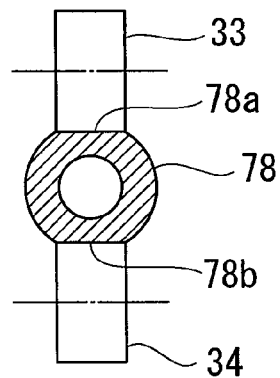
FIG. 10 is a view showing an example of a cross section of the insertion-section where the insertion-section is pressed by rollers.

As shown in FIG. 10, several portions of the outer surface of the insertion-section may be cut off so that several portions of the cross section are linear. It is preferable that outer surfaces of the rollers 33, 34 may contact the cut-off sections 78a and 78b formed on the insertion-section 78.

At least one of the above modifications (including the guide member 32) can improve transmission of the rotation force produced by the rollers 33 and 34 to the insertion-section reliably; thus, it is possible to move the insertion-section in a desirable direction.

A second embodiment of the present invention is explained in details as follows with reference to the drawings. The same reference numerals are added to the same elements as those shown in the first embodiment. Duplicate explanations are omitted if already explained previously in the first embodiment.

The present embodiment is characterized in that two pairs of rollers are provided so that the insertion-section and the wire are driven independently.

Figure 11:
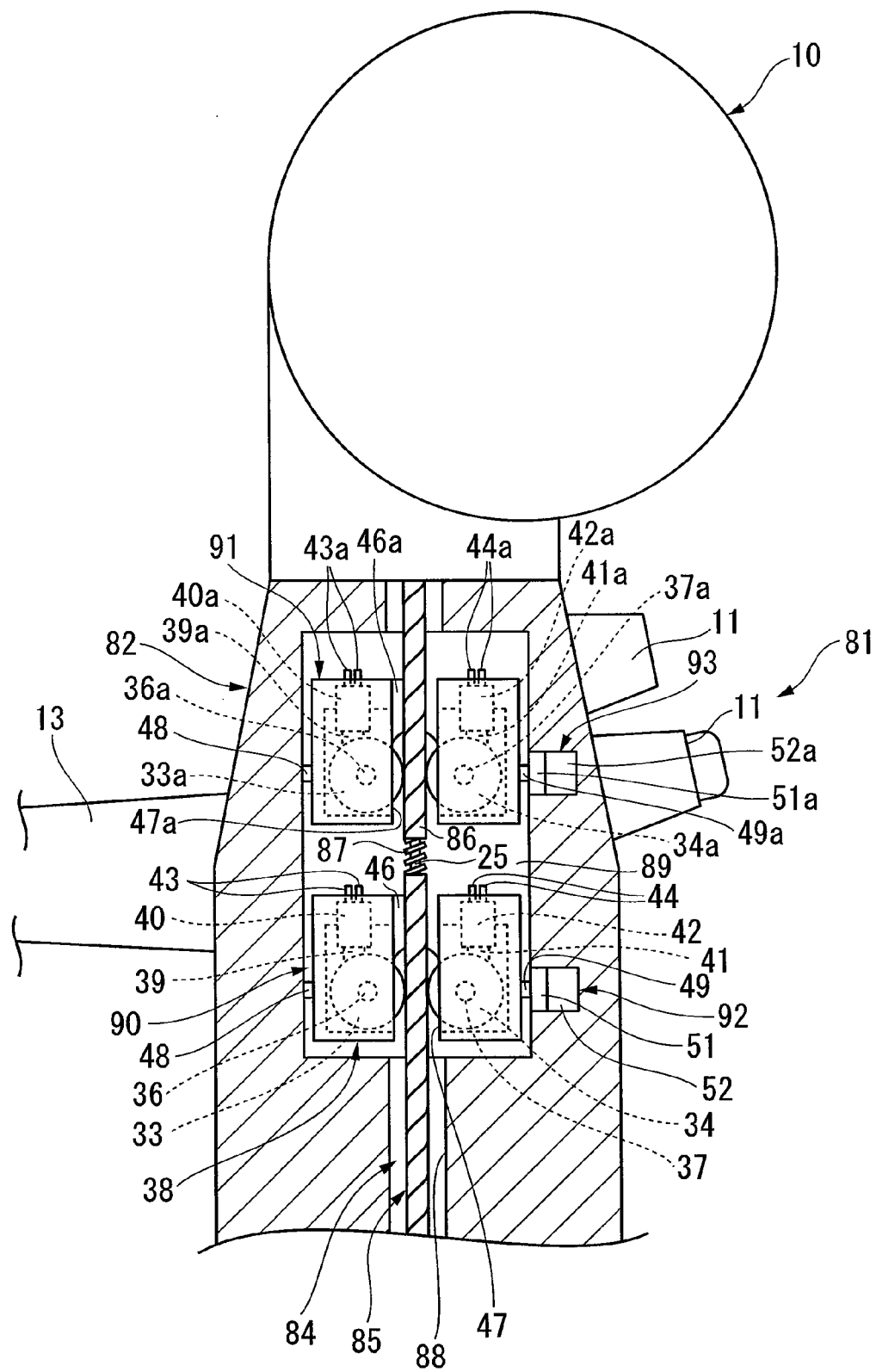
FIG. 11 is a part of a cross section of the endoscope system according to embodiments of the present invention where the driving-section corresponds to the first direction.

As shown in FIG. 11, an instrument 84 has a flexible insertion-section 85. The treating section 22 is connected to a distal end of the insertion-section 85 (see FIG. 1). The treating section 22 is driven by feeding or windging the wire 25. The wire 25 is inserted in the insertion-section 85 and extracted from a proximal end of the insertion-section 85. A flexible tube 86 is fixed to the extracted portion of the wire 25 so that the extracted portion is covered by the tube 86 having approximately the same outer diameter as that of the insertion-section 85. A flexible member 87 wound in a coil-manner connects a distal end of the tube 86 and a proximal end of the insertion-section 85.

An operation section 82 is disposed on the proximal end of the insertion section 3 (see FIG. 1) of an endoscope 81. An instrument channel 88 is disposed in the insertion section 3, and in the operation section 82. Switches 11, knobs 12 (see FIG. 1), and a universal cable 13 are disposed on the operation section 82. A driving-section-enclosing section 89, i.e., an enlarged space formed in the instrument channel 88, is disposed in the operation section 82. An driving-section 90 (first driving section) and a wire driving section 91 (second driving section) are disposed, in order from bottom side to top side in FIG. 11, in the driving-section-enclosing section 89. A first pivoting section 92 is connected to the driving-section 90. A second pivoting section 93 is connected to the wire driving section 91.

The driving-section 90 performs extending, retracting, and rotating of the inserting the insertion-section 85. The driving-section 90 is rotatively supported by the first pivoting section 92 in the operation section 82. Structures of the driving-section 90 and the first pivoting section 92 are the same as the driving-section 35 and the pivoting section 50 of the first embodiment. The motors 40 and 42 have brakes, e.g., electromagnetic brakes.

The wire driving section 91 is disposed nearer the proximal end of the operation section 82 by a predetermined length than the driving-section 90. The wire driving section 91 inserts and retracts the insertion-section 85. The wire driving section 91 also feeds and winds the wire 25. The wire driving section 91 is rotatively supported by the second pivoting section 93 in the operation section 82. Structures of the wire driving section 91 and the second pivoting section 93 are the same as the driving-section 35 and the pivoting section 50 of the first embodiment. Reference numerals indicating elements forming the wire driving section 91 and the second pivoting section 93 have "a" after the reference numerals for the purpose of identification. The motors 40a and 42a have brakes, e.g., electromagnetic brakes. The distance between the wire driving section 91 and the driving-section 90 is determined in order that the rollers 33, 34 contained in the driving-section 90 are pressed against the insertion-section 85, and that the rollers 33a, 34a contained in the wire driving section 91 are pressed against the tube 86, while the instrument 84 is inserted in the instrument channel 88.

Figure 12:
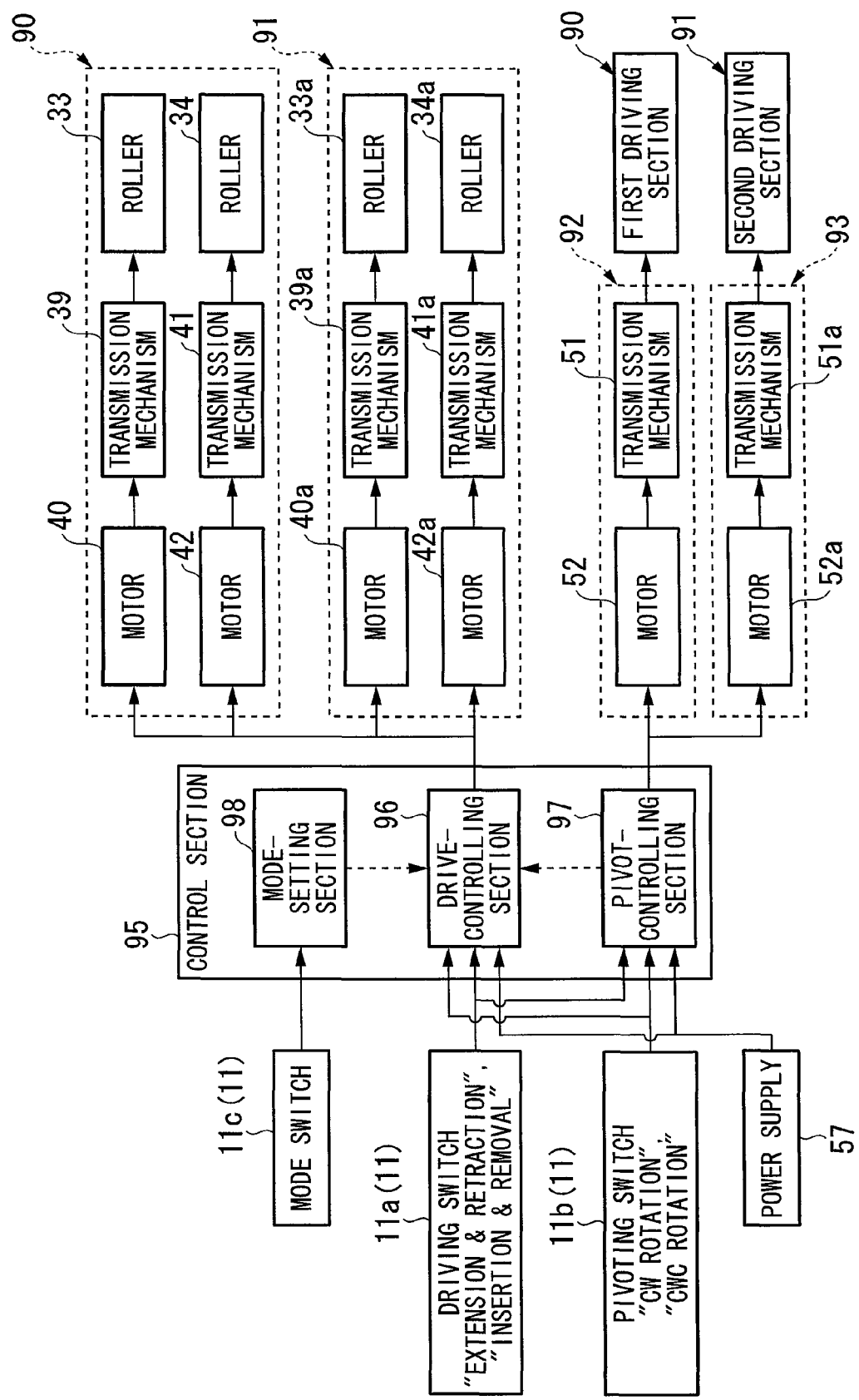
FIG. 12 is a control block diagram according to the present invention.

FIG. 12 is a block diagram for controlling the endoscope system of the present embodiment.

The driving switch 11a can perform "inserting the instrument 84 into the instrument channel 88", "retracting the instrument 84 from the instrument channel 88", "extending the instrument 84 through the instrument channel 7", and "retracting the instrument 84 through the instrument channel 7". The driving switch 11a is connected to a drive-controlling-section (driver circuit) 96 and a pivot-controlling-section (driver circuit) 97 which are contained in a control section 95.

The pivoting switch 11b can perform "clockwise rotation of the instrument 84", "counterclockwise rotation of the instrument 84", "clockwise rotation of the insertion section 85", "counterclockwise rotation of the insertion section 85", "clockwise rotation of the wire 25", and "counterclockwise rotation of the wire 25". The pivoting switch 11b is connected to the drive-controlling-section 96 and the pivot-controlling-section 97 in the control section 95.

One of the switches 11 formed on the operation section 82 is a mode switch 11c. Three modes can bee selected by the mode switch 11c, i.e., first driving mode in which the driving-section 90 and the wire driving section 91 are driven synchronously, second mode in which only the wire driving section 91 is driven, and third mode in which only the driving-section 90 is driven. The mode switch 11c is connected to a mode setting section 98. The mode setting section 98 supplies signals to the drive-controlling-section 96 in accordance with the selected mode.

The drive-control-section 96 is connected to the power supply 57, and to four motors 40, 42, 40a, and 42a. The drive-control-section 96 can control rotational directions of the rollers 33, 34, 33a, and 34a. Parameters for controlling the rotational directions of the rollers 33, 34, 33a, and 34a are a direction of the instrument 84 determined by the operator of the endoscope, positions thereof to be rotated, rotational directions, rotative angles of the pivoting sections 92 and 93, and information with respect to modes which will be explained later.

The drive-control-section 97 is connected to the power supply 57; and two motors 50 and 52a. The drive-control-section 96 receives information with respect to the direction of the driving-section 90; and information with respect to the direction of the wire driving section 91 from a pivot-controlling-section 97.

Operations in the present embodiment are explained as follows. An initial mode of the mode switch 11c is a first driving mode. The insertion-section 85 is extracted from the instrument channel 88, and most of it is wound in the enclosure device 10. In this state, both the driving-section 90 and the wire driving section 91 support the distal end of the insertion-section 85.

The instrument 84 is inserted into the instrument channel 88 by disposing the driving-section 90 and the wire driving section 91 in a direction parallel with the extension/retraction direction of the instrument 84, i.e., in the first direction; and turning the driving switch 11a on so that the insertion is conducted. The drive-control-section 96 drives the motors 40 and 42 contained in the driving-section 90; and motors 40a and 42a contained in the wire driving section 91. The drive-control-section 96 rotates the rollers 33 and 33a in the clockwise direction and rotates the rollers 34 and 34a in the counterclockwise direction. By doing this, the instrument 84 (and the insertion-section 85), supported between the rollers 33, 34 and between the rollers 33a, 34a, is fed toward a distal end of the endoscope 81. The motors 40, 42, 40a and 42a are stopped after a predetermined length of the treating section 22 protrudes from the distal end of the endoscope 81. In this state, the rollers 33, 34 contained in the driving-section 90 are pressed against the insertion-section 85. Also, the rollers 33a, 34a contained in the wire driving section 91 are pressed against the tube 86.

The driving switch 11a is turned to a mode corresponding to the retraction movement in the case that the instrument 84 is retracted from the instrument channel 88. The rollers 33, 34, 33a, and 34a rotate opposite to the feeding direction so that the insertion-section 85 is retracted and wound into the enclosure device 10. The distal end of the insertion-section 85 is not wound into the enclosure device 10.

Extending and retracting of the instrument 84 with respect to the object section can be conducted similarly to the insertion and retraction of the insertion-section 85.

The wire 25 can be fed to the distal end of the instrument 84 while the instrument 84 is inserted in the instrument channel 88 by setting the mode switch 11c in a second driving mode and setting the driving switch 11a in a mode corresponding to the feeding direction. The drive-control-section 96 receives information indicating the second driving mode from the mode setting section 98. The drive-control-section 96 rotates only the rollers 33a and 34a contained in the wire driving section 91. Accordingly, the tube 86 supported between the rollers 33a, 34a is fed so that the wire 25 is fed to the distal end of the instrument 84. The drive-control-section 96 brakes the motors 40 and 42 contained in the driving-section 90 electrically so that the insertion-section 85 does not move to the distal end of the instrument 84.

By doing this, only the wire 25 is fed to the distal end of the instrument 84; thus, a pair of the gripping members open, e.g., 24a, 24b as shown in FIG. 1. The driving switch 11a is turned to a mode to conduct the retraction in the case that the wire 25 is retracted. By doing this, the rollers 33a and 34a make reverse rotations; thus, the wire 25 is retracted. As explained previously, since the insertion-section 85 does not move, only the wire 25 is wound. Therefore, as a result of that, a pair of the gripping members, e.g., 24a and 24b close.

Figure 13:
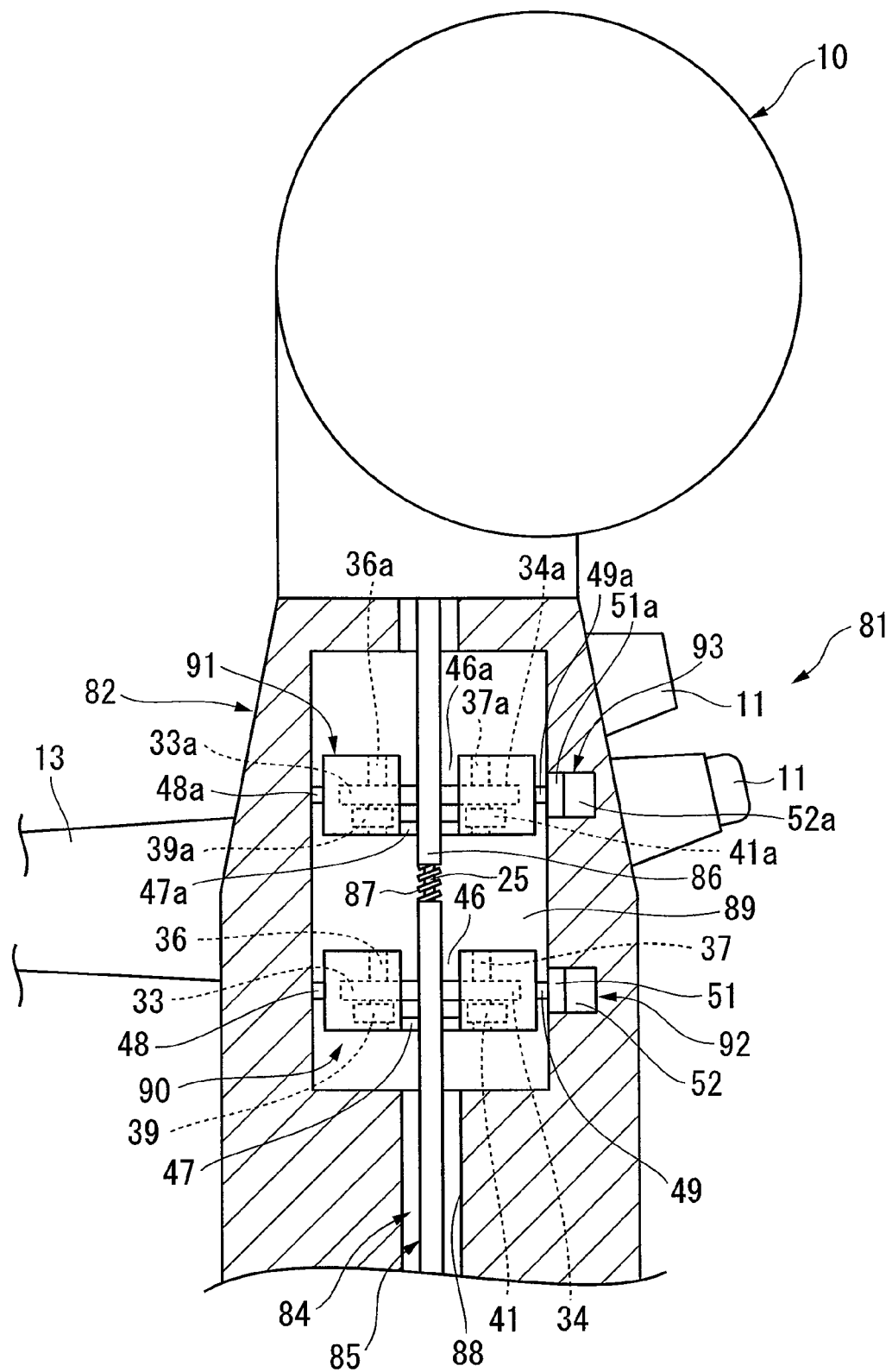
FIG. 13 is a part of a cross section of the endoscope system according to embodiments of the present invention where the driving-section corresponds to the second direction.

The pivoting switch 11b is turned on after setting the mode switch 11c to the first driving mode in the case that the overall instrument 84 is rotated around its axial line in the clockwise direction (or counterclockwise direction) from this state. By doing this, the pivot-controlling-section 97 drives the motor 52 contained in the first pivoting section 92 and the motor 52a contained in the second pivoting section 93 synchronously in the same direction; thus the first pivoting section 92 and the second pivoting section 93 rotate by 90 degrees. As shown in FIG. 13, the driving-section 90 and the wire driving section 91 are disposed in the second direction so that the rotational directions of the rollers 33, 34, 33a, and 34a contained in these sections 90 and 91 are orthogonal to the extension/retraction directions of the instrument 84. After that, the drive-control-section 96 rotates the rollers 33, 34 contained in the driving-section 90 and the rollers 33a, and 34a contained in the wire driving section 91 synchronously; thus, the insertion-section 85 and the tube 86 (including the wire 25) rotate together.

In the case that the wire 25 is rotated around its axial line while the insertion-section 85 is not rotated around its axial line, the mode switch 11c is turned to the second driving mode and the driving switch 11b is turned to conduct a clockwise rotation or a counterclockwise rotation. The drive-control-section 96 receives information sent from the mode setting section 98 and rotates only the motors 41a and 42a contained in the wire driving section 91. By doing this, the tube 86 and the wire 25, connected to each other, rotate. If the treating section disposed at a distal end of the wire 25 is a basket, the wire 25 rotates the basket. In this state, since the drive-control-section 96 brakes the motors 40 and 42 contained in the driving-section 90 electrically, the insertion-section 85 does not rotate.

In the case that the insertion-section 85 is rotated around its axial line while the wire 25 is fixed, the mode switch 11c is turned to a third driving mode and the driving switch 11b is turned to conduct a clockwise rotation or a counterclockwise rotation. By doing this, the insertion-section 85 is rotated by the driving-section 90. Since the motors 40a and 42a contained in the wire driving section 91 are braked electrically, the wire 25 does not rotate.

Controlling the pivot-controlling-section 97 is skipped when only the rotation direction of the instrument 84, etc., around its axial direction is changed since the first pivoting section 92 or the second pivoting section 93 is in the second direction; thus, only the drive-controlling-section 96 carries out its function. Also, only the drive-control-section 96 carries out its function when the modes are changed and rotational directions are changed.

When the driving switch 11a is turned on while the first pivoting section 92 and the second pivoting section 93 are disposed in the second direction, the drive-control-section 96 changes directions of the first pivoting section 92 and the second pivoting section 93 in the first direction by driving the motors 52 disposed in the pivoting section 51 and the motor 52a contained in the pivoting section 51a. After changing the directions of the first pivoting section 92 and the second pivoting section 93, the drive-control-section 96 rotates the rollers 33, 34, 33a, and 34a into the required directions.

According to the present embodiment, the endoscope system permitting the instrument 84 to move electrically has two driving sections and two pivoting sections. Therefore, it is possible to drive the insertion-section 85 and the wire 25 synchronously or independently. Therefore, various movements can be realized, e.g., extending/retracting the instrument 84; opening/closing the gripping members, e.g., 24a and 24b as shown in FIG. 1 by feeding/winding the wire 25; and rotating only a distal end section of the instrument 84 by rotating the wire 25.

A third embodiment of the present invention is explained in details as follows with reference to the drawings. The same reference numerals are added to the same elements as those shown in the first and second embodiments. Also, duplicate explanations are omitted if already explained previously in the first and second embodiments.

Figure 14:
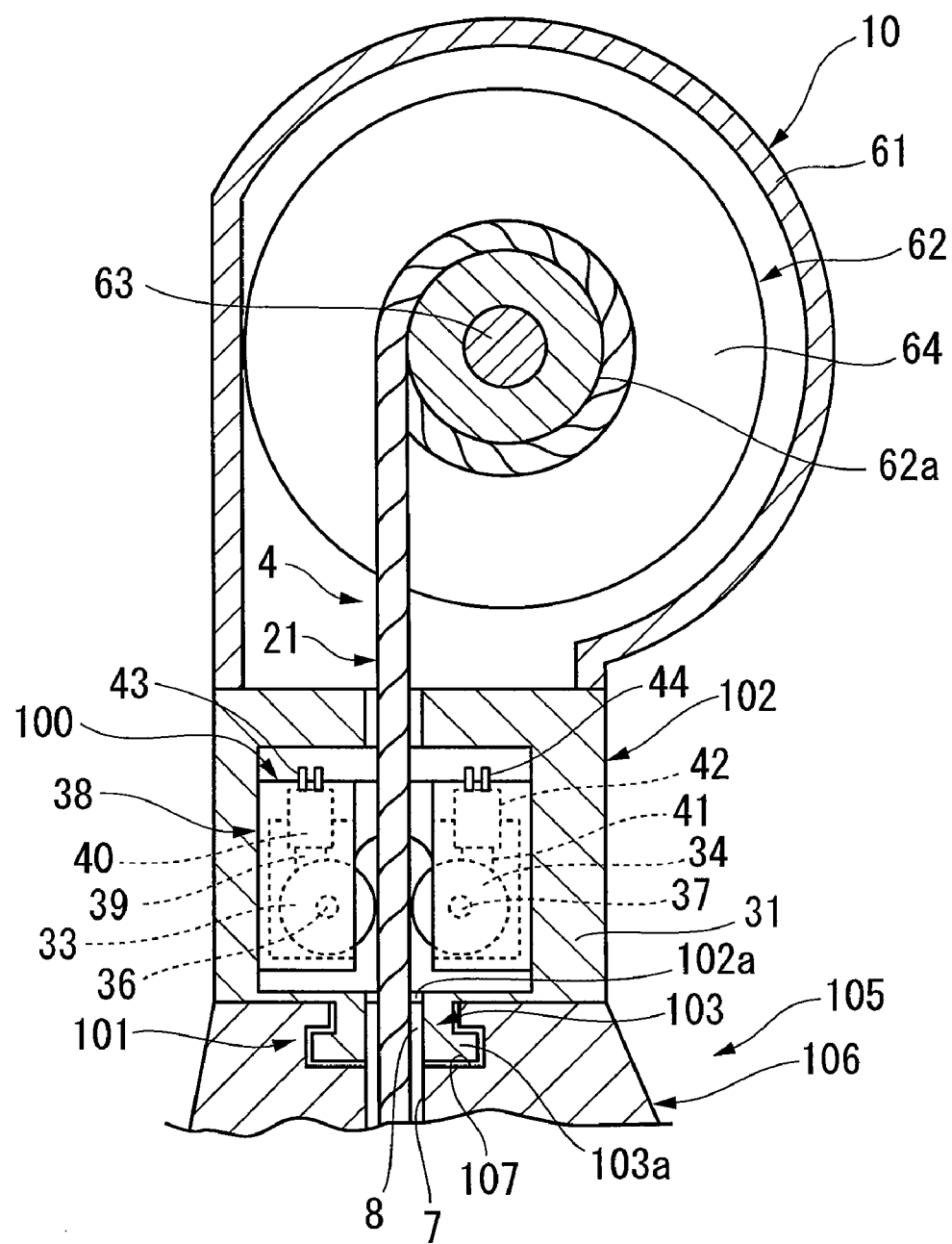
FIG. 14 is a part of a cross section of the endoscope system according to embodiments of the present invention.

As shown in FIG. 14, an endoscope 105 in the present embodiment has a rotative-connective section 101 by which it is possible to rotate an driving-section 100 manually.

The rotative-connective section 101 includes an engaging body 103 (male-engaging section) protruding around an aperture 102a formed on an instrument-extension-retraction device 102; and an engaging section 107 (female-engaging section) formed around the insertion port 8 of the instrument channel 7 disposed on the proximal end of an operation section 106 in the endoscope 105.

The diameter of the engaging body 103, extending along an axial line of the instrument-extension-retraction device 102 increases in a direction in which the axial direction and a distal end section 103a cross each other. distal end There is a space in the engaging body 103 so that the insertion-section 21 can be inserted therein; and the instrument-extension-retraction device 102 can rotate around the axial line of the instrument channel 7.

The engaging section 107 (female-engaging section) has a female-engaging shape with which the engaging body 103 can engage.

The structure of the driving-section 100 is the same as that shown in the first embodiment except that the roller supporting section 38 is fixed to the housing 31 directly. A control section (not shown in the drawing) for controlling the driving-section 100 has the drive-controlling-section 56 as shown in FIG. 4. The drive-controlling-section 56 controls the rotation of the motors 40 and 42 in accordance with the mode selected by the driving switch 11a.

In this endoscope system, the driving-section 100 is driven so as to extend/retract the instrument 4. Details of the extension/retraction movement are the same as those explained with respect to the first embodiment.

The motors 40 and 42 are stopped and the instrument-extension-retraction device 102 is rotated manually with respect to the operation section 106 so as to rotate the instrument 4 around its axial line while the insertion-section 21 is inserted in the instrument channel 7. The instrument-extension-retraction device 102 rotates around the axial line of the instrument channel 7 by the rotative-connective section 101. Also, the driving-section 100 fixed to the instrument-extension-retraction device 102 rotates around the axial line of the instrument channel 7. Since the motors 40 and 42 are braked electrically in this state, the insertion-section 21 supported between a pair of the rollers 33 and 34 contained in the driving-section 100 rotates with the instrument-extension-retraction device 102.

Since the axial line of the instrument 4 and the axial line of the instrument channel 7 coincide approximately, the instrument 4 rotates around its axial line by rotating the driving-section 100.

According to the present embodiment, since the instrument-extension-retraction device 102 is rotative desirably with respect to the operation section 106 of the endoscope 105, it is possible to rotate the instrument 4 manually by a simple structure.

Although the instrument-extension-retraction device 102 is engaged to an inside of the operation section 102, i.e., the female-engaging section, the instrument-extension-retraction device 102 may be engaged to an outside of the operation section 106 rotatively.

The rotative-connective section 101 may be formed by gears disposed around the engaging body 103 and motors disposed in the operation section 106. By doing this, it is possible to rotate the instrument-extension-retraction device 102 with respect to the operation section 106 by the rotating force of the motors.

The instrument-extension-retraction device 102 may be formed by fixing the driving-section 90 and the wire driving section 91 to the housing 31 directly as shown in FIG. 11. In this state, it is possible to extend/retract the instrument 84 with the wire 25. Also, it is possible to rotate the instrument 84 around its axial line using the rotative-connective section 101.

The present invention is not limited to the above embodiments, i.e., the present invention can be applied to various aspects.

For example, the first embodiment may not use the guide member 32. Also, the second and third embodiment may use the guide member 32.

The instrument-extension-retraction device 9 of the first embodiment may be fixed to the operation section 2 unitarily. Also, the instrument-extension-retraction device 9 of the first embodiment may be detachable from the operation section 2. If the instrument-extension-retraction device 9 is detachable, it is possible to exchange various instruments in accordance with treatments to be performed.

The motors 40, 42, 40a, and 42 contained in the driving-sections 35, 90, 91, and 100 may be connected to rotation axes (36, 37, 36a, and 37a) of the rollers (33, 34, 33a, and 34a) directly.

A freely-rolling ball may be used for replacing one of the rollers, e.g., 33, 34, 33a and 34a. Also, the driving-sections 35, 90, 91, and 100 may be formed by a linear motion mechanism using solenoid devices. The linear motion mechanism supports the solenoid devices movably with respect to the extension/retraction direction of the instruments. The solenoid devices have pressing sections for pressing the insertion-section 21 so that the pressing sections are movable toward the insertion-section 21. The solenoid devices can be moved toward a distal end of the instrument while the pressing sections expand to make contact with the insertion-section 21. After the pressing sections are separated from the insertion-section 21, the solenoid devices can be retracted by the linear motion mechanism. By repeating these movements, it is possible to extend/retract the insertion-section 21. The pressing sections may be of a rigid material or expandable balloons.

In order to increase contact between the driving-sections 35, 90, 91 and 100 and the guide member 32, a frictional force produced by pressing the guide member to the driving-sections may be used.

The instrument is extended and retracted by the driving-section in the endoscope system according to the present invention. Therefore, driving direction of the insertion-section can be changed by changing the driving-section. Therefore, it is possible to extend the instrument from the channel, retract the instrument into the channel, and rotate the instrument around the axial line of the instrument easily.

What is claimed is:

1. An endoscope system comprising:
    an endoscope having a channel;
    an insertion-section flexibly inserted into the channel;
    a treating section, disposed at a distal end of the insertion-section, for treating a target section;
    a driving-section, making contact with the insertion-section, for driving the insertion-section along predetermined directions; and
    a pivoting section for directing the driving-section toward a first direction or a second direction, wherein
    the first direction is a direction in which the insertion-section is driven along an axial line of the insertion-section,
    the second direction is a direction in which the insertion-section rotates around the axial line,
    the driving-section has a plurality of rollers making contact with the insertion-section, and
    the pivoting section is configured to allow rotation of the plurality of rollers around an axis which is orthogonal to the axial line and to an axial line of the plurality of rollers.

2. An endoscope system according to claim 1, wherein the pivoting section directs the driving-section from 0 to 90 degrees with respect to the axial line.

3. An endoscope system according to claim 1, wherein the driving-section comprises: the plurality of rollers; and a switching section for changing the rotational direction of at least one of the rollers in accordance with a pivoted direction of the rollers.

4. An endoscope system according to claim 1, wherein protrusions are formed on outer surfaces of the rollers.

5. An endoscope system according to claim 1, further comprising:
    a housing for pivotably supporting the driving-section; and
    a guide member, fixed in the housing, through which the insertion-section is inserted, the guide member having apertures through which the driving-section making contact with the insertion-section.

6. An endoscope system according to claim 1, wherein protrusions and grooves are alternately provided on a surface of the insertion-section, the surface making contact with the driving-section.

7. An endoscope system according to claim 1, wherein a cross section of a part of the insertion-section is polygonal, the part making contact with the driving-section.

8. An endoscope system according to claim 1, wherein the pivoting section has a pivoting shaft having a pivoting axial line, the pivoting axial line being disposed on a line extending along radial directions of the rollers, and passes through a section in which the rollers contact with the insertion-section.

* * * * *